US007608625B2

(12) United States Patent
Miyawaki et al.

(10) Patent No.: US 7,608,625 B2
(45) Date of Patent: Oct. 27, 2009

(54) METHOD FOR TREATING BRUXISM AND BRUXISM-RELATED DISEASES

(75) Inventors: Shouichi Miyawaki, Kagoshima (JP); Teruko Yamamoto, Okayama (JP)

(73) Assignee: Eisai R & D Management Co., Ltd., Tokyo (JP)

( * ) Notice: Subject to any disclaimer, the term of this patent is extended or adjusted under 35 U.S.C. 154(b) by 0 days.

(21) Appl. No.: 10/547,796

(22) PCT Filed: Jan. 30, 2004

(86) PCT No.: PCT/JP2004/000939

§ 371 (c)(1),
(2), (4) Date: Sep. 6, 2005

(87) PCT Pub. No.: WO2004/080487

PCT Pub. Date: Sep. 23, 2004

(65) Prior Publication Data

US 2006/0173045 A1 Aug. 3, 2006

(30) Foreign Application Priority Data

Mar. 13, 2003 (JP) ............................. 2003-068755

(51) Int. Cl.
*A61K 31/44* (2006.01)
*A61K 31/425* (2006.01)
(52) U.S. Cl. ...................... 514/292; 514/370
(58) Field of Classification Search .................. 514/292, 514/370
See application file for complete search history.

(56) References Cited

U.S. PATENT DOCUMENTS

| 4,255,431 | A | 3/1981 | Junggren et al. |
| 4,628,098 | A | 12/1986 | Nohara et al. |
| 4,758,579 | A | 7/1988 | Kohl et al. |
| 4,808,596 | A | 2/1989 | Matsuishi et al. |
| 5,045,552 | A | 9/1991 | Souda et al. |
| 5,840,910 | A | 11/1998 | Souda et al. |
| 5,916,904 | A | 6/1999 | Sato et al. |
| 5,948,789 | A | 9/1999 | Larsson et al. |
| 5,998,445 | A | 12/1999 | Souda et al. |
| 6,063,782 | A | 5/2000 | Kimura et al. |
| 6,426,369 | B1 | 7/2002 | Sato et al. |
| 6,740,667 | B2 | 5/2004 | Sato et al. |

FOREIGN PATENT DOCUMENTS

| WO | WO 94/28923 A1 | 12/1994 |
| WO | WO 01/62290 A2 | 8/2001 |

OTHER PUBLICATIONS

Bartlett et al., Drugs of Today (1998), 34(3): 231-239.*
Cross et al., Annals of Pharmacotherapy, (May, 2002) 36(5), pp. 912-916.*
Chase et al., Mental Health Aspects of Developmental Disabilities, (2002), 5(2), pp. 34-45.*
Rogers et al., Am. J. Ment. Retardation, (Mar. 1992), 96(5):522-7 (abstract).*
Shaw et al., ASDC J. Dent. Child., 65(6), (Nov.-Dec. 1998), pp. 484-486.*
Bell et al., Aust. Dent. J., 47(1), (Mar. 2002), pp. 30-35.*
Abstract of Katayama, A., et al., "Effect of Gastric-Acid-Inhibiting Drugs on Rhythmic Masticatory Muscle Activity," presented at the $82^{nd}$ *General Session and Exhibition of the IADR*, accessible online at http://iadr.confex.com/iadr/2004Hawaii/techprogram/abstract_44719.htm on Nov. 27, 2003.
Lavigne G.J., Manzini, C., "Bruxism" In: Kryger MH, Roth T, Dement WC, editors. *Principles and Practice of Sleep Medicine*. Philadelphia: W.B. Saunders, 2000, 773-785.
Lobbezoo, F., et al., "The Effect of the Catecholamine Precursor L-Dopa on Sleep Bruxism: A Controlled Clinical Trial," *Movement Disorders* 12:73-78, Movement Disorder Society (1997).
Miyawaki, S., et al., "Association Between Nocturnal Bruxism and Gastroesophageal Reflux," *Sleep* 26:888-892, Associated Professional Sleep Societies, LLC (Nov. 2003).
Patent Abstracts of Japan, English language abstract for JP 01-290628 A, (1989).
Patent Abstracts of Japan, English language abstract for JP 02-022225 A, (1990).
*The Merck Manual*, $17^{th}$ *Edition*, Merck Research Laboratories, Chapter 20, pp. 232-233 (1999).
Miyawaki, S., et al., "Association between nocturnal bruxism and gastroesophageal reflux," presented at $81^{st}$ General Session of the IADR, Sweden, 4 pages (Jun. 27, 2003).
Abstract published in *J. Dent. Res.* 82:B-296, Abstract No. 2284, International and American Associations for Dental Research (Jun. 2003; published online Feb. 25, 2003).
Becht, J.L. and T.D. Byars, "*Gastroduodenal ulceration in foals,*" *Equine Vet J.*, 18: 307-12, Equine Veterinary Journal Ltd, Cambs, UK, (July 1986).
Cuypers, J. et al., "*Therapy of cluster headache with histamine H1 and H2 receptor antagonists,*" *Eur Neurol*: 18: 345-7, S. Karger AG, Basel (Jan. 1979).
Dieckmann, M. And E. Deegen, "*Magenulzera beim Pferd—klinische und gastroskopische Befunde bei 12 Pferden (1989-1990)*" ["*Stomach ulcers in the horse—clinical and gastroscopic findings in 12 horses (1989-1990)*"], Tierarztl Prax: 19(4): 386-394, Schattauer, (Aug. 1991).
E.L. Spierings, "*Headache of gastrointestinal origin: case studies,*" Headache: 42(3): 217-9, Wiley InterScience (Mar. 2002).

(Continued)

*Primary Examiner*—Frederick Krass
*Assistant Examiner*—Sara E Clark
(74) *Attorney, Agent, or Firm*—Sterne, Kessler, Goldstein & Fox P.L.L.C.

(57) ABSTRACT

The present invention provides a preventive or therapeutic agent for bruxism or bruxism-related diseases that contains as an active ingredient at least one selected from the group consisting of proton pump inhibitors, histamine $H_2$ receptor antagonists, and acid pump antagonists. Examples of the proton pump inhibitors include rabeprazole, omeprazole, esomeprazole, lansoprazole, pantoprazole, or tenatoprazole, or salts thereof, or hydrates thereof.

6 Claims, 3 Drawing Sheets

OTHER PUBLICATIONS

K. Taniyama, from Chapter 9 of "New Pharmacodynamics revised fourth edition," C. Tanaka and R. Kato., eds., Nankodo Co., Ltd., Tokyo, Japan, publishers, pp. 452-454 (2002).

Partial English translation of document NPL16: K. Taniyama, from Chapter 9 of "New Pharmacodynamics revised fourth edition," C. Tanaka and R. Kato., eds., Nankodo Co., Ltd., Tokyo, Japan, publishers, pp. 452-454 (2002).

* cited by examiner

METHOD FOR TREATING BRUXISM AND BRUXISM-RELATED DISEASES

This application is a 35 U.S.C. 371 (national stage) application of PCT/JP04/00939, filed Jan. 30, 2004.

TECHNICAL FIELD

The present invention relates to a preventive or therapeutic agent for bruxism, and more particularly to a preventive or therapeutic agent for bruxism and bruxism-related diseases that contains a drug that suppresses gastroesophageal reflux as an active ingredient.

BACKGROUND ART

Bruxism is thought to involve parafunction, abnormal oral habit or parasomnia. Bruxism can have a serious effect on health, as it causes such conditions as dental attrition and tooth fracture, pain and discomfort in masticatory muscle, and temporomandibular disorders.

Although occlusion was previously thought to be involved in the onset of bruxism, it has recently become clear that occlusion is hardly involved at all in the onset of this condition (for example, see the non-patent reference 1).

To date, treatment for bruxism has only involved such splint (Nightguard) therapy as insertion of a splint similar to a boxing mouthpiece that prevents the upper and lower teeth from touching, cognitive behavioral therapy to train the individual to consciously prevent the involuntary movements, biofeedback therapies, and pharmacotherapies. Of these, the splint therapy is extremely expensive and questionable in terms of its effectiveness. With pharmacotherapies, there have been reports that an anxiolytic agent such as diazepam, a tricylic antidepressant, a muscle relaxant, and L-dopa are effective as a preventive or therapeutic agent for bruxism (for example, see non-patent reference 2). However, none of these methods provide a fundamental therapy for bruxism. Therefore, there is a strong need for an effective and fundamental therapy for bruxism.

[Non-Patent Reference 1]
Lavigne G. J, Manzini C. Bruxism. In: Kryger M H, Roth T. and Dement W, eds. Principles and practice of sleep medicine. Philadelphia: W B Saunders, 2000: 773-85.

[Non-Patent Reference 2]
Lobbezoo F, Lavigne G J, Tanguay R, and Montplaisir J Y. Mov Disord 12: 73-78, 1997.

DISCLOSURE OF INVENTION

An object of the present invention is to provide an effective and fundamental preventive or therapeutic agent for bruxism and bruxism-related diseases.

The present inventors focused attention on that gastroesophageal reflux causes sleep bruxism, and have hypothesized that bruxism may be prevented or treated if gastroesophageal reflux can be prevented. In light of the above circumstances, the present inventors therefore focused their research on the prevention or treatment of bruxism, and have discovered for the first time that an agent that inhibits gastric acid secretion, as typified by a proton pump inhibitor, is useful in the prevention or treatment of bruxism and bruxism-related diseases, and completed the present invention through further research.

Thus, the present invention provides:

(1) a preventive or therapeutic agent for bruxism comprising an inhibitor of gastric acid secretion as an active ingredient;

(2) a preventive or therapeutic agent for bruxism comprising at least one selected from the group consisting of a proton pump inhibitor, a histamine $H_2$ receptor antagonist, or an acid pump antagonist as an active ingredient;

(3) a preventive or therapeutic agent for bruxism comprising a proton pump inhibitor and a histamine $H_2$ receptor antagonist as an active ingredient;

(4) a preventive or therapeutic agent for bruxism comprising a proton pump inhibitor as an active ingredient;

(5) the preventive or therapeutic agent according to any one of (2) to (4), wherein the proton pump inhibitor is rabeprazole, omeprazole, esomeprazole, lansoprazole, pantoprazole or tenatoprazole, or a salt of the foregoing, or hydrate of the foregoing;

(6) the preventive or therapeutic agent according to any one of (2) to (4), wherein the proton pump inhibitor is rabeprazole or a salt thereof;

(7) the preventive or therapeutic agent according to any one of (2) to (4), wherein the proton pump inhibitor is a sodium salt of rabeprazole;

(7-1) the preventive or therapeutic agent according to any one of (2) to (4), wherein the proton pump inhibitor is omeprazole or a salt thereof;

(7-2) the preventive or therapeutic agent according to any one of (2) to (4), wherein the proton pump inhibitor is esomeprazole or a salt thereof;

(7-3) the preventive or therapeutic agent according to one of (2) to (4), wherein the proton pump inhibitor is lansoprazole;

(7-4) the preventive or therapeutic agent according to any one of (2) to (4), wherein the proton pump inhibitor is pantoprazole or a salt thereof;

(8) the preventive or therapeutic agent according to (2) or (3) wherein the histamine $H_2$ receptor antagonist is cimetidine, ranitidine, famotidine, roxatidine, nizatidine or lafutidine, or a salt of the foregoing;

(9) a preventive or therapeutic agent for bruxism-related diseases comprising an inhibitor of gastric acid secretion as an active ingredient;

(10) a preventive or therapeutic agent for bruxism-related diseases comprising at least one selected from the group consisting of a proton pump inhibitor, a histamine $H_2$ receptor antagonist, or an acid pump antagonist as an active ingredient;

(11) a preventive or therapeutic agent for bruxism-related diseases comprising a proton pump inhibitor and a histamine $H_2$ receptor antagonist as an active ingredient;

(12) a preventive or therapeutic agent for bruxism-related diseases comprising a proton pump inhibitor as an active ingredient;

(13) the preventive or therapeutic agent according to any one of (10) to (12), wherein the proton pump inhibitor is rabeprazole, omeprazole, esomeprazole, lansoprazole, pantoprazole or tenatoprazole, or a salt of the foregoing, or hydrate of the foregoing;

(14) the preventive or therapeutic agent according to any one of (10) to (12), wherein the proton pump inhibitor is rabeprazole or a salt thereof;

(15) The preventive or therapeutic agent according to any one of (10) to (12), wherein the proton pump inhibitor is a sodium salt of rabeprazole;

(15-1) the preventive or therapeutic agent according to any one of (10) to (12), wherein the proton pump inhibitor is omeprazole or a salt thereof;

(15-2) the preventive or therapeutic agent according to any one of (10) to (12), wherein the proton pump inhibitor is esomeprazole or a salt thereof;

(15-3) the preventive or therapeutic agent according to any one of (10) to (12), wherein the proton pump inhibitor is lansoprazole;

(15-4) the preventive or therapeutic agent according to any one of (10) to (12), wherein the proton pump inhibitor is pantoprazole or a salt thereof;

(16) the preventive or therapeutic agent according to (10) or (11), wherein the histamine $H_2$ receptor antagonist is cimetidine, ranitidine, famotidine, roxatidine, nizatidine or lafutidine, or a salt of the foregoing;

(17) the preventive or therapeutic agent according to any one of (9) to (16), wherein the bruxism-related disease is temporomandibular disorders, tooth hypersensitivity, occlusal trauma, dental attrition, wedge-shaped defects of tooth, gingival recession, tooth fracture, tooth mobility, root resorption, alveolar bone resorption, masseter muscle hypertrophy, masticatory muscle pain, breakage of tooth crown restoration, falling of tooth crown restoration, or headache; and (18) the preventive or therapeutic agent according to any one of (9) to (16), wherein the bruxism-related disease is temporomandibular arthrosis.

Further, the present invention provides:

(19) a method for preventing or treating bruxism comprising administering an inhibitor of gastric acid secretion in an effective amount;

(20) a method for preventing or treating bruxism-related diseases comprising administering an inhibitor of gastric acid secretion in an effective amount;

(21) a method for preventing or treating temporomandibular disorders comprising administering an inhibitor of gastric acid secretion in an effective amount;

(22) a use for an inhibitor of gastric acid secretion for the manufacture of a preventive or therapeutic agent for bruxism;

(23) a use for an inhibitor of gastric acid secretion for the manufacture of a preventive or therapeutic agent for bruxism-related diseases; and (24) a use for an inhibitor of gastric acid secretion for the manufacture of a preventive or therapeutic agent for temporomandibular arthrosis.

BRIEF DESCRIPTION OF DRAWINGS

FIG. 2 (A) shows temporal muscle activity during sleep (4 hours) in a bruxism patient, after placebo medication (left drawings) and a proton pump inhibitor ("PPI") medication (right drawings).

FIG. 2 (B) shows the frequency of bruxism episodes (**P<0.0001) (left drawing) and duration of bruxism episodes (*P<0.001) (right drawing) per hour of sleep in groups of the bruxism patients (n=8) after placebo and a proton pump inhibitor medications.

BEST MODE FOR CARRYING OUT THE INVENTION

Below, the present invention is described in detail through the definitions of symbols and terminology used in this specification and the mode for carrying out the invention.

The term "preventive or therapeutic agent" used herein is defined as including single agent and multiple agents. Multiple agents are defined as agents that are obtained either by formulating single agent separately or by formulating single agent simultaneously and are administered simultaneously or at fixed intervals useful for prevention or treatment.

The term "inhibitor of gastric acid secretion" used herein is defined as a drug that inhibits the secretion of gastric acid. Examples of inhibitors of gastric acid secretion include, but are not limited to, a proton pump inhibitor, a histamine $H_2$ receptor antagonist, an acid pump antagonist, an anticholinergic agent, a cholinesterase inhibitor, a gastrin antagonist, an antacid, traditional Chinese medicines such as a scopolia extract or a herbal medicine extract, or the like.

The term "proton pump inhibitor" used herein is defined as a drug that modifies the SH group of the proton pump ($H^+$, $K^+$-ATPase) to inhibit the enzyme activity and suppress acid secretion. Proton pump inhibitors are usually defined as compounds with a benzimidazole or an imidazopyridine skeleton. Examples of proton pump inhibitors include, but are not limited to, rabeprazole (I), omeprazole (II), esomeprazole (III), lansoprazole (IV), pantoprazole (V), or tenatoprazole (VI), the chemical structures of which are shown below, or salts thereof or hydrates thereof. Of these, the preferable proton pump inhibitors include rabeprazole (I) or a sodium salt thereof, omeprazole (II) or a sodium salt thereof, esomeprazole (III) or a magnesium salt thereof, lansoprazole (IV), or pantoprazole (V) or a sodium salt thereof. It is more preferably to use the sodium salt of rabeprazole (I).

-continued

Rabeprazole can be prepared according to the method described in the specification of U.S. Pat. No. 5,045,552, omeprazole can be prepared according to the method described in the specification of U.S. Pat. No. 4,255,431, esomeprazole can be prepared according to the method described in the specification of U.S. Pat. No. 5,948,789, lansoprazole can be prepared according to the method described in the specification of U.S. Pat. No. 4,628,098, pantoprazole can be prepared according to the method described in the specification of U.S. Pat. No. 4,758,579, and tenatoprazole can be prepared according to the method described in the specification of U.S. Pat. No. 4,808,596.

The term "histamine $H_2$ receptor antagonist" used herein is defined as a drug that selectively blocks the histamine $H_2$ receptor in the parietal cells of the gastric mucosa so as to suppress gastric acid secretion. Examples of histamine $H_2$ receptor antagonists include, but are not limited to, cimetidine, ranitidine, famotidine, roxatidine, nizatidine, or lafutidine, or salts thereof. In general, ranitidine is used as ranitidine hydrochloride, while roxatidine is used as roxatidine acetate hydrochloride.

The term "acid pump antagonist" used herein is defined as a drug that suppresses acid secretion by reversibly blocking the proton pump. Examples of acid pump antagonists include, but are not limited to, the compound described in the specification of U.S. Pat. No. 6,063,782 or the like.

The term "salt" used herein can include, for example, a salt of an inorganic acid, a salt of an organic acid, a salt of an inorganic base, a salt of an organic base, or a salt of an acidic or basic amino acid. It is more preferably to use pharmacologically acceptable salt.

Examples of the salts of inorganic acids include hydrochloride, hydrobromide, sulfate, nitrate, and phosphate, and examples of the salts of organic acids include acetate, succinate, fumarate, maleate, tartrate, citrate, lactate, stearate, benzoate, methanesulfonate, ethanesulfonate, and p-toluene sulfonate.

Examples of the salts of inorganic bases include an alkali metal salt such as sodium salt and potassium salt, an alkali earth metal salt such as calcium salt and magnesium salt, aluminum salt, and ammonium salt. Examples of the salts of organic bases include diethylamine, diethanolamine, meglumine, and N,N'-dibenzylethylenediamine.

The term "bruxism-related diseases" used herein is defined as a disease caused by bruxism. Examples of bruxism-related diseases include, but are not limited to, temporomandibular disorders, tooth hypersensitivity, occlusal trauma, dental attrition, wedge-shaped defects of tooth, gingival recession, tooth fracture, tooth mobility, root resorption, alveolar bone resorption, masseter muscle hypertrophy, masticatory muscle pain, breakage of tooth crown restoration, falling of tooth crown restoration, or headache. Of these, temporomandibular disorders can be described as a good example.

The term "temporomandibular disorders" used herein refers to a group of chronic disorders with the main symptom of pain in the temporomandibular joint (TMJ) or masticatory muscle, TMJ sounds such as clicking and crepitus, difficulty of jaw-opening, or abnormal jaw movements. The clinical condition of temporomandibular disorders includes masticatory muscle disorder, capsular ligament disorder, TMJ disk disorder, and osteoarthritis.

The administration route and dose when the proton pump inhibitor is administered to the patients as the preventive or therapeutic agent for bruxism or bruxism-related diseases vary depending on such factors as the patient's symptoms, type and degree of severity of the ulcer or gastritis, age, and heart, liver, and kidney function, and there are no restrictions thereon. In general, the proton pump inhibitor is orally administered at a dose of 0.01-100 mg per day for an adult patient.

More specifically, the daily adult dose of rabeprazole is preferably 0.1-10 mg if the sodium salt of rabeprazole is administered. The daily adult dose for omeprazole is preferably 0.1-20 mg. The daily adult dose for esomeprazole is preferably 0.1-20 mg if the magnesium salt of esomeprazole is administered. The daily adult dose of lansoprazole is preferably 0.1-30 mg. The daily adult dose for pantoprazole is preferably 0.1-40 mg if the sodium salt of pantoprazole is administered.

The administration route, dose, and number of doses when the histamine $H_2$ receptor antagonist is administered for the patient as the preventive or therapeutic agent for bruxism or bruxism-related diseases vary depending on such factors as the patient's symptoms, type and degree of severity of the ulcer or gastritis, age, and heart, liver, and kidney function, and there are no restrictions thereon.

In general, the histamine $H_2$ receptor antagonist is orally administered at a dose of 1-800 mg per day for an adult patient.

More specifically, the daily adult dose of cimetidine is preferably 1-800 mg or more preferably 50-400 mg. The daily adult dose for ranitidine is preferably 5-300 mg if ranitidine hydrochloride is administered, or more preferably 30-150 mg. The daily adult dose for famotidine is preferably 1-40 mg or more preferably 5-20 mg. The daily adult dose of roxatidine is preferably 5-150 mg if roxatidine acetate hydrochloride is administered, or more preferably 25-75 mg. The daily adult dose for nizatidine is preferably 30-300 mg or more preferably 50-150 mg. The daily adult dose of lafutidine is preferably 0.5-20 mg or more preferably 2.5-10 mg.

Examples of dosage form can include a powder, a fine granule, a granule, a tablet, and a capsule. When formulating the drug, it is possible to manufacture by the conventional method using a common carrier. However, since as the proton pump inhibitor is particularly unstable, a more stable preparation can be achieved using the methods described in Japanese Patent Laid-open Publication No. H1-290628 and Japanese Patent Laid-open Publication No. H2-22225.

When preparing a solid formulation for oral use by the conventional method, an excipient is added to the active ingredient, if necessary, after a binder, a disintegrant, a lubricant, a colorant, and other agents are further added to the active ingredient, the drug is prepared using the conventional method into the powder, the fine granule, the granule, the tablet, the capsule, or other dosage form.

Examples of the excipient include lactose, cornstarch, sucrose, glucose, mannitol, sorbit, crystalline cellulose, silicon dioxide and the like. Examples of the binder include polyvinyl alcohol, polyvinyl ether, ethylcellulose, methylcellulose, gum arabic, hydroxypropylcellulose, hydroxypropylmethylcellulose, polyvinylpyrrolidone and the like. Examples of the disintegrant include starch, crystalline cellulose, calcium carbonate, sodium bicarbonate, calcium citrate, dextrin, pectin, calcium carboxymethylcellulose and the like. Examples of the lubricant include magnesium stearate, talc, silica and the like. Examples of the colorant include substances approved as additives to pharmaceuticals. Of course, a sugar coating or other suitable coating for other purposes can be applied to the tablet and the granule.

Furthermore, according to the present invention, a combination of the proton pump inhibitor and the histamine $H_2$ receptor antagonist can be administered to the patient as the preventive or therapeutic agent for bruxism and bruxism-related diseases.

There are no particular restrictions on the combination of the proton pump inhibitor and the histamine $H_2$ receptor antagonist that can be administered, but the proton pump inhibitor and histamine $H_2$ receptor antagonist may be combined at the time of administration. This type of combination can include, for example, 1) administration of a preparation obtained by simultaneously formulating the proton pump inhibitor and the histamine $H_2$ receptor antagonist, 2) simultaneous administration of two types of preparation obtained by separately formulating the proton pump inhibitor and the histamine $H_2$ receptor antagonist, or 3) the administration at certain intervals effective for the prevention or treatment of bruxism and bruxism-related diseases of two types of preparation obtained by separately formulating the proton pump inhibitor and the histamine $H_2$ receptor antagonist (for example, administration of the proton pump inhibitor followed by the histamine $H_2$ receptor antagonist, or administration in the reverse order).

When the proton pump inhibitor and the histamine $H_2$ receptor antagonist are administered in combination, the dose percentage of each drug type can be appropriately selected in accordance with various factors, including the patient's age, body weight, sex, degree of symptom severity, administration mode, and the specific disease type. For example, the dose percentage of the proton pump inhibitor and the histamine $H_2$ receptor antagonists is usually 10:1-1:400 by weight, or preferably within the range 2:1-1:200.

EXAMPLES

Examples and experiments are shown below in order to demonstrate the advantageous effects of the present invention, but these are only examples and the present invention is not limited to these particular examples. Those skilled in the art can execute the present invention by appropriately modifying the conditions described in the examples below and any such changes are included within the scope of the claims in the present patent application.

Experiment 1

Figure 1:
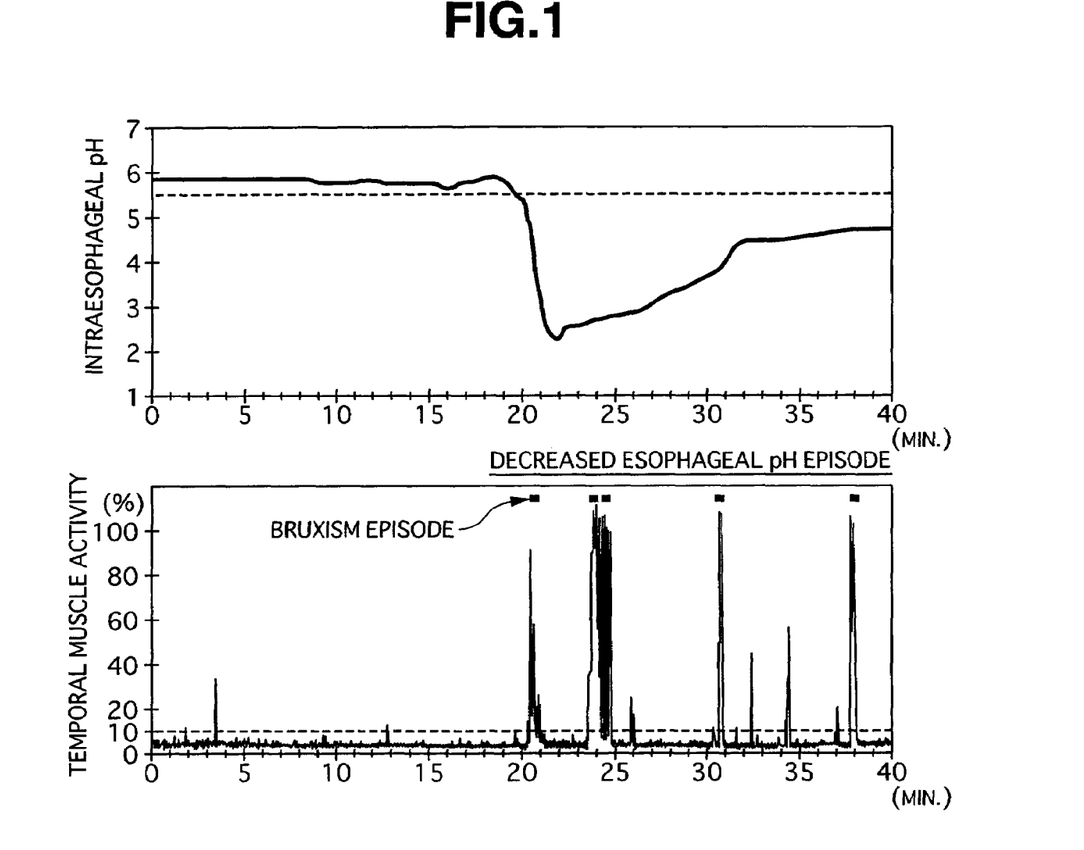
FIG. 1 shows (A) intraesophageal pH changes and (B) temporal muscle activity, during sleep (40 minutes) in a bruxism patient.

Measurement of temporal muscle activity and intraesophageal pH change during sleep in the bruxism patient Methods A catheter with a pH electrode was inserted into the test subject's esophagus 5 cm above the upper portion of the lower esophageal sphincter and pH was measured while the subject was asleep, while a disposable (bipolar) electrode was affixed to the skin at the front of the temporal muscle on one side. An amount of muscle activity during sleep was measured from 2.5 hours after falling asleep for a 40-minute period. At the same time, video and sound recordings were made that confirmed bruxism during sleep. FIG. 1 shows the results. In this Figure, when stable pH levels in the esophagus declined sharply, this was defined as an "decreased esophageal pH episode".

Results

According to the results shown in FIG. 1, jaw motion accompanying rhythmic masticatory muscle activity (bruxism episode) was observed at high frequency during a period corresponding to "decreased esophageal pH episode".

Experiment 2

Measurement of temporal muscle activity during sleep in the bruxsim patient medicated with placebo or the proton pump inhibitor Methods In a double-blind trial, test subjects were assigned to either medication with placebo or the proton pump inhibitor [sodium salt of rabeprazole (10 mg; brand name: Pariet (registered trademark), Eisai Co., Ltd.)] and, according to the method used in experiment 1, the amount of muscle activity during sleep in the front of the temporal muscle on one side was measured for a 4-hour period between 1 and 5 hours after falling asleep. Video and sound recordings were made at the same time that confirmed bruxism during sleep. The results are shown in FIG. 2(A).

Results

Figure 2:
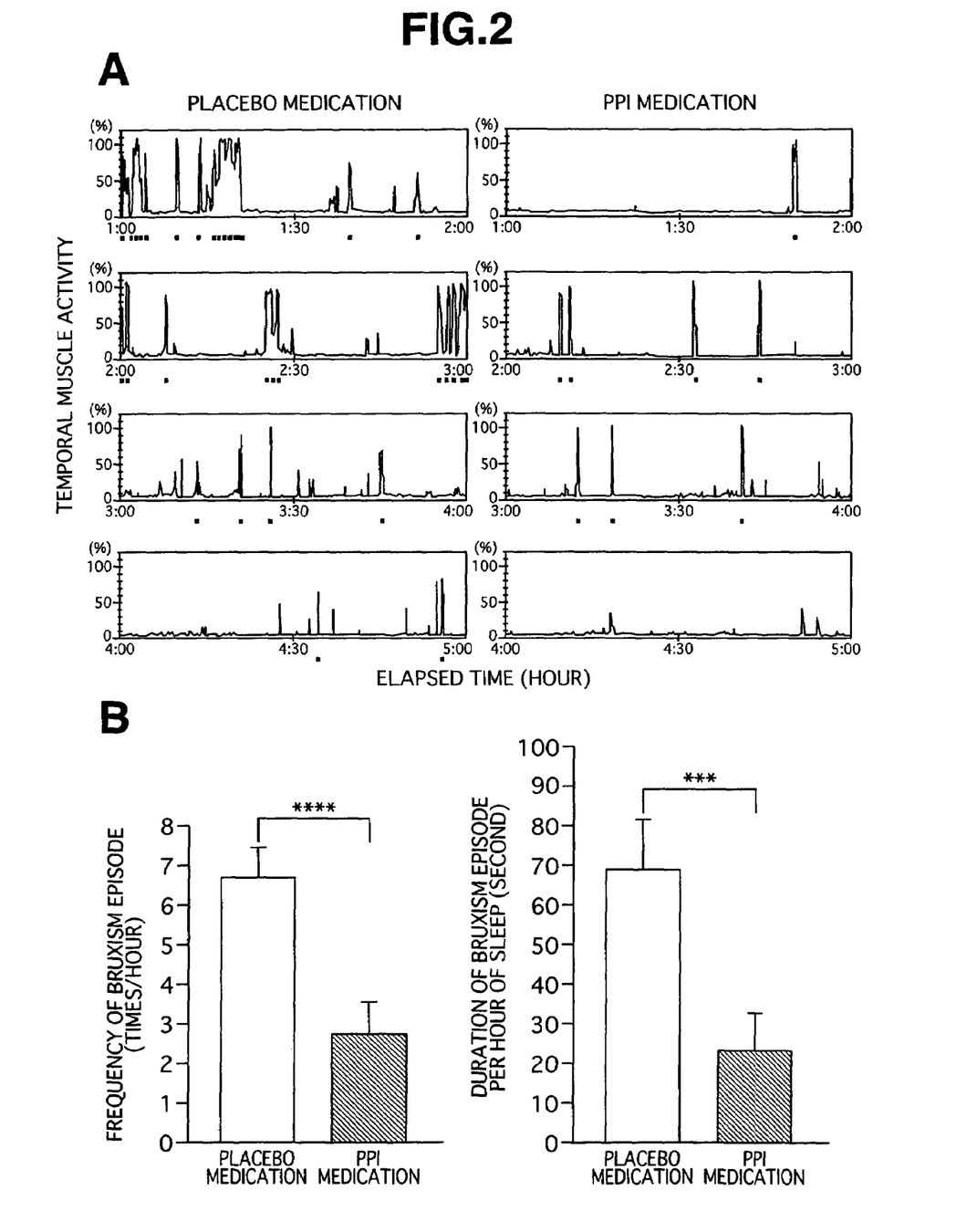

The results in FIG. 2(A) demonstrate that, as compared to placebo, the medication with the proton pump inhibitor generated a substantial decline in the frequency of jaw motion accompanying rhythmical temporal muscle activity (bruxism episode).

Further, FIG. 2(B) shows the frequency and duration of bruxism episodes per hour in groups of the bruxism patients (n=8) after medication with placebo or the proton pump inhibitor. A paired t test was used to test for significance, with $P<0.05$ defined as indicating a statistically significant difference.

The results in FIG. 2(B) demonstrate that medication with the proton pump inhibitor significantly reduces the frequency and duration of bruxism episodes.

Experiment 3

Measurement of the frequency of jaw movement accompanying rhythmic masticatory muscle activity (bruxism episode) during sleep in the bruxism patient medicated with (1) placebo, (2) the proton pump inhibitor, (3) the histamine $H_2$ receptor antagonist, and (4) a combination of the proton pump inhibitor and the histamine $H_2$ receptor antagonist Methods In a double-blind trial, the test subjects were medicated with (1) placebo, (2) the proton pump inhibitor [sodium salt of rabeprazole (10 mg; brand name: Pariet (registered trademark), Eisai Co., Ltd.)], (3) the histamine $H_2$ receptor antagonist [famotidine (10 mg; brand name: Gaster (registered trademark), Yamanouchi Pharmaceutical Co., Ltd.)], and (4) the combination of the proton pump inhibitor [sodium salt of rabeprazole (10 mg)] and the histamine $H_2$ receptor antagonist [famotidine (10 mg)], with both drugs administered simultaneously in the case of group (4). According to the methods used in experiment 1, the amount of muscle activity during sleep in the front of the temporal muscle on one side was measured for a 4-hour period between 1 and 5 hours after falling asleep. Video and sound recordings were made at the same time and confirmed bruxism during sleep.

Results

Figure 3:
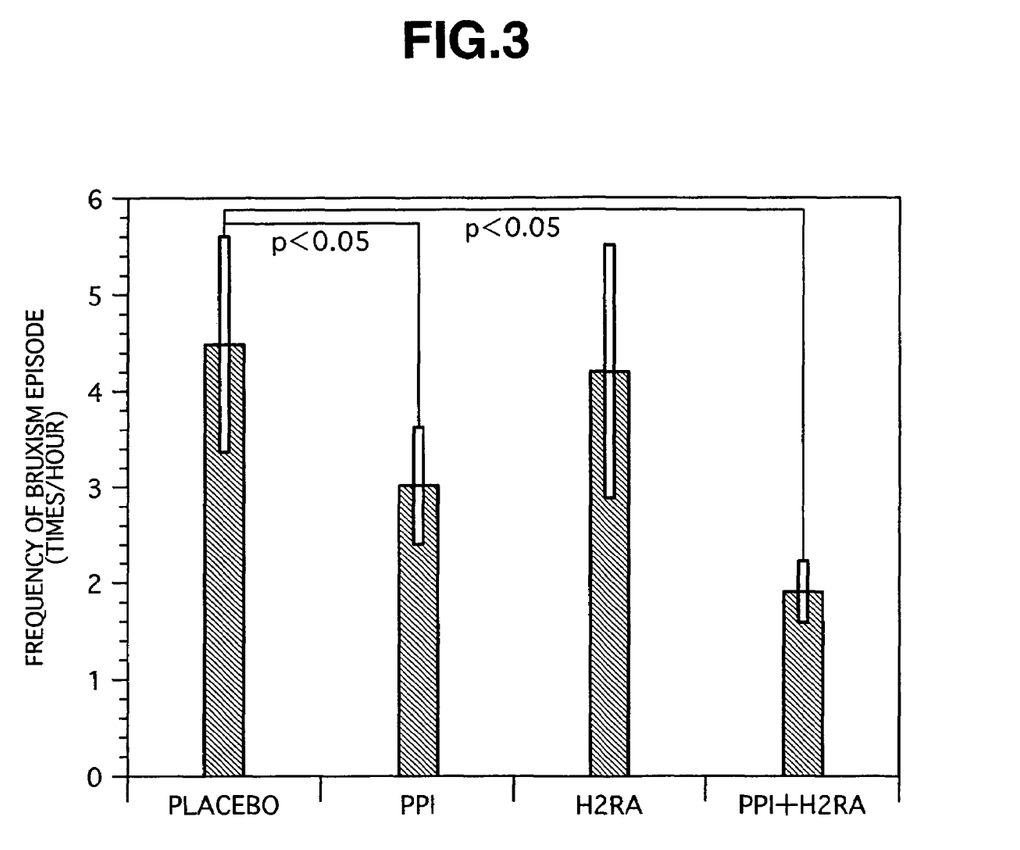
FIG. 3 shows the frequency of bruxism episodes per hour of sleep in groups of the bruxsim patients (n=9), (1) after placebo medication, (2) after PPI medication, (3) after a histamine $H_2$ receptor antagonist ($H_2$RA) medication, and (4) after PPI in combination with $H_2$RA medication.

FIG. 3 shows the frequency of bruxism episodes per hour in groups of the bruxism patients (n=9) after medication with (1) placebo, (2) the proton pump inhibitor, (3) the histamine $H_2$ receptor antagonist, and (4) the combination of the proton pump inhibitor and the histamine $H_2$ receptor antagonist. A paired t test was used to test for significance, with P<0.05 defined as indicating a statistically significant difference.

The largest reduction in the frequency of bruxism episodes was observed in the group medicated with the combination of the proton pump inhibitor and the histamine $H_2$ receptor antagonist, followed in order by the group medicated with the proton pump inhibitor and the group medicated with the histamine $H_2$ receptor antagonist.

Furthermore, as compared to the placebo group, there was a significant reduction in bruxism episodes in the group medicated with the combination of the proton pump inhibitor and the histamine $H_2$ receptor antagonist and in the group medicated with the proton pump inhibitor.

INDUSTRIAL APPLICABILITY

An agent that inhibits gastric acid secretion according to the present invention, as exemplified by the proton pump inhibitor, acts to suppress gastroesophageal reflux that induces bruxism and are extremely useful in the effective and fundamental prevention or treatment of bruxism and bruxism-related diseases.

In addition, according to the present invention, the cost of treating bruxism and bruxism-related diseases (especially the cost involved in splint therapy) can be substantially reduced.

We claim:

1. A method for treating bruxism, said method comprising administering rabeprazole or a salt thereof in an amount effective to treat said bruxism to a bruxism patient.

2. A method for treating bruxism, said method comprising administering rabeprazole or a salt thereof and famotidine or a salt thereof in an amount effective to treat said bruxism to a bruxism patient.

3. A method for treating a bruxism-related disease in a bruxism patient, said method comprising administering rabeprazole or a salt thereof to said bruxism patient in an amount effective to treat said bruxism-related disease, wherein said bruxism-related disease is selected from the group consisting of temporomandibular disorders, tooth hypersensitivity, masseter muscle hypertrophy, masticatory muscle pain, and headache.

4. A method for treating a bruxism-related disease in a bruxism patient, said method comprising administering rabeprazole or a salt thereof and famotidine or a salt thereof to said bruxism patient in an amount effective to treat said bruxism-related disease, wherein said bruxism-related disease is selected from the group consisting of temporomandibular disorders, tooth hypersensitivity, masseter muscle hypertrophy, masticatory muscle pain, and headache.

5. A method for treating a temporomandibular disorder in a bruxism patient, said method comprising administering rabeprazole or a salt thereof to said patient in an amount effective to treat said temporomandibular disorder.

6. A method for treating a temporomandibular disorder in a bruxism patient, said method comprising administering rabeprazole or a salt thereof and famotidine or a salt thereof in an amount effective to treat said temporomandibular disorder.

* * * * *

UNITED STATES PATENT AND TRADEMARK OFFICE
CERTIFICATE OF CORRECTION

PATENT NO.        : 7,608,625 B2                                                Page 1 of 1
APPLICATION NO.   : 10/547796
DATED             : October 27, 2009
INVENTOR(S)       : Miyawaki et al.

It is certified that error appears in the above-identified patent and that said Letters Patent is hereby corrected as shown below:

<u>Cover Page</u>

Item (73), Assignee, replace "Eisai R&D Management Co., Ltd., Tokyo (JP)" with --Eisai R&D Management Co., Ltd., Tokyo (JP); Shouichi Miyawaki, Kagoshima (JP); Teruko Yamamoto, Okayama (JP)--.

Signed and Sealed this

Seventh Day of September, 2010

David J. Kappos
*Director of the United States Patent and Trademark Office*